(12) United States Patent
Yuki et al.

(10) Patent No.: US 6,506,956 B1
(45) Date of Patent: Jan. 14, 2003

(54) MOLD CAPABLE OF DEGRADING DIOXIN, DEGRADATION OF DIOXIN WITH THE USE OF THE SAME, METHOD FOR PRODUCING COMPOSTS CAPABLE OF DEGRADING DIOXIN AND METHOD FOR GROWING PLANTS

(75) Inventors: Junichiro Yuki, Tokyo (JP); Motoshi Suzuki, Tokyo (JP); Hideo Miyamoto, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 09/674,278

(22) PCT Filed: Apr. 27, 1999

(86) PCT No.: PCT/JP99/02242

§ 371 (c)(1),
(2), (4) Date: Oct. 30, 2000

(87) PCT Pub. No.: WO99/55834

PCT Pub. Date: Nov. 4, 1999

(30) Foreign Application Priority Data

Apr. 28, 1998 (JP) .......................................... 10-117707

(51) Int. Cl.⁷ .............................. A62D 3/00; C12P 1/02
(52) U.S. Cl. .............................. 588/207; 435/171; 71/8
(58) Field of Search ................................. 588/205, 206, 588/207; 435/171; 71/8

(56) References Cited

U.S. PATENT DOCUMENTS

| | | | | |
|---|---|---|---|---|
| 4,642,131 A | * | 2/1987 | Hoitink | 424/93.3 |
| 4,891,320 A | * | 1/1990 | Aust et al. | 435/262 |
| 4,900,348 A | * | 2/1990 | Hoitink | 71/6 |
| 5,874,275 A | * | 2/1999 | Berka et al. | 435/200 |
| 5,877,014 A | * | 3/1999 | Shetty et al. | 435/262.5 |
| 5,989,889 A | * | 11/1999 | Rey et al. | 435/225 |
| 6,033,891 A | * | 3/2000 | Golightly et al. | 435/190 |

FOREIGN PATENT DOCUMENTS

| | | | | |
|---|---|---|---|---|
| JP | 9-225450 | * | 9/1997 | B09C/1/10 |
| JP | 10-257895 | * | 9/1998 | C12N/15/09 |
| JP | 10-323646 | * | 12/1998 | B09B/3/00 |

* cited by examiner

Primary Examiner—Stanley S. Silverman
Assistant Examiner—Eileen E. Nave
(74) Attorney, Agent, or Firm—Oblon, Spivak, McClelland, Maier & Neustadt, P.C.

(57) ABSTRACT

The invention provides lignin-degradable fungi capable of degrading dioxins that have accumulated in the soil for farm crops, into harmless substances; a method for degrading dioxins by applying the fungi to a dioxin-containing object to such a degree that the cell concentration in the object reaches at least $1 \times 10^2$ cfu per gram of the object; compost containing the fungi; a method for producing compost that comprises a step of thermally fermenting a lignin-containing, plant-derived organic material to be compost, at a temperature falling between 65 and 100° C. for at least 2 hours, followed by inoculating the thus-fermented material with lignin degrading enzymes-producing fungi and further fermenting it; and a method of using the compost for cultivating plants.

20 Claims, No Drawings

MOLD CAPABLE OF DEGRADING DIOXIN, DEGRADATION OF DIOXIN WITH THE USE OF THE SAME, METHOD FOR PRODUCING COMPOSTS CAPABLE OF DEGRADING DIOXIN AND METHOD FOR GROWING PLANTS

TECHNICAL FIELD

The present invention relates to fungi having dioxin degradability, to a method of using the fungi for degrading dioxins, to compost that contains the fungi, to a method for producing the compost, and to a method of using the compost for cultivating plants. More precisely, the invention relates to fungi capable of degrading dioxins having accumulated in the soil of farms and developed lands into harmless substances, to a method of using the fungi for degrading dioxins, to compost that contains the fungi, to an effective method for producing the compost, and to a method of using the compost for cultivating plants for agricultural crops, etc.

BACKGROUND ART

Dioxins are a type of harmful substances that are discharged in the nature from various facilities, appliances and others typically including incinerators for garbage and industrial wastes.

Known are various dioxins of different chemical structures, and 2,3,7,8-tetrachlorodibenzo-p-dioxin is the most typical. Living organisms could hardly degrade dioxins, and many of them absorbs dioxins. Through food chain, dioxins are finally accumulated and concentrated in animals, often causing malformation in the animal kingdom, and the problem with dioxins is now a grave object of public concern.

Various methods for preventing the generation of dioxins have been investigated and proposed. For example, a two-stage method of burning exhaust gas at high temperatures in automobiles and incinerators has been put into practical use. However, this is still insufficient for preventing the generation of dioxins. Dioxins having been discharged in air fall down on the earth along with rain and snow, and accumulate in soil. At present, no one knows an effective method for degrading dioxins into harmless substances.

Some recent studies are directed to biodegradation of chemical substances such as dioxins and others that are hardly degraded in the nature, and some reports say that lignin degrading enzymes produced by a type of microorganisms can degrade dioxins [BIO INDUSTRY, Vol. 15, No. 2, pp. 5–13 (1998); Chemistry, Vol. 52, No. 10, pp. 24–25 (1997)].

Relative to the degradation of dioxins by such microorganisms-derived lignin degrading enzymes, the reports precisely say that the lignin degrading enzymes produced by white rot fungi, which are in a group of wood-rotting fungi of the genus Basidiomycetes, have the ability to degrade various chemical substances including dioxins, further saying that the white rot fungi grow with a nutrient source of polysaccharides, cellulose and hemicellulose that are the essential ingredients of wood, and degrade lignin in wood depending on the energy from the nutrient source. Accordingly, in wooded regions where such white rot fungi live, dioxins having fallen down on the earth along with rain shall be degraded by lignin degrading enzymes produced by the white rot fungi.

In farms for agricultural crops, grass, etc., however, the soil is poor in cellulose and hemicellulose that are to be the nutrient source for white rot fungi. In addition, a large amount of microbicides and chemical fertilizers are often applied to the soil of such farms. Therefore, the environment of farms is not suitable for white rot fungi living therein. In some area of lands developed by civil engineering, trees and flowers are planted. However, the soil in the area is also poor in cellulose and hemicellulose, and its environment is not suitable for white rot fungi living therein.

Accordingly, dioxins will accumulate increasingly in such farms and developed lands, and the influence of the thus-accumulated dioxins on living organisms will be a more serious problem. In that situation, it is much desired to develop a technique effective for degrading the dioxins having accumulated in the soil of farms and developed lands into harmless substances to thereby renew the soil so that the renewed soil may have no negative influence on living organisms.

The present invention is to provide fungi having the ability to degrade dioxins that have accumulated in the soil where agricultural crops and others are cultivated into harmless substances, to provide compost that contains the fungi and a method of producing the compost, and to provide a method of using the compost for cultivating plants.

DISCLOSURE OF THE INVENTION

We, the present inventors have assiduously studied to solve the problems noted above, and, as a result, have found that, when a plant-derived organic material that contains lignin is used for producing compost and when the plant-derived organic material having been thermally fermented under a specific condition is inoculated with a specific type of fungi to be compost, then the resulting compost can degrade dioxins having accumulated in the soil of farms and others into harmless substances. On the basis of these findings, we have completed the present invention.

Specifically, the subject matter of the invention resides in the following:

1. Fungi having the ability to degrade lignin and belonging to the genera, Chaetomium, Penicillium and Schizophyllum, which have the ability to degrade dioxins.

2. A method of degrading dioxins, which comprises applying the fungi of above 1 to a dioxin-containing organic or inorganic substance in an amount of at least $1 \times 10^2$ cfu per gram of the dry weight of the substance.

3. A method of degrading dioxins by applying the fungi of above 1 to a dioxin-containing organic or inorganic substance, for which is used a material inoculated with the fungi.

4. Compost containing the fungi of above 1.

5. The method of degrading dioxins as in above 3, wherein the fungi-inoculated material is the compost of above 4.

6. A method for producing the compost of above 4 by fermenting a plant-derived organic material, which is characterized in that the plant-derived organic material contains lignin, and the plant-derived organic material having been thermally fermented in a process that includes a step of keeping it at a temperature falling between 65 and 100° C. for at least 2 hours is further fermented while being inoculated with at least one type of the fungi of above 1 at a temperature not higher than 65° C.

7. A method for producing the compost of above 4, wherein the plant-derived organic material is inoculated with the fungi of above 1 to such that the cell concentration in the inoculated material is at least $1 \times 10^2$ cfu per gram of the dry weight of the plant-derived organic material.

8. A method for producing the compost of above 4, wherein the plant-derived organic material is thermally fermented in the presence of a nitrogen fertilizer component-containing substance that serves as a fermentation promoter, in the initial stage of the process of thermophilic fermentation.

9. Compost having the ability to degrade dioxins, in which the cell concentration of the fungi of above 1 falls between $1 \times 10^3$ and $1 \times 10^{10}$ cfu per gram of the dry weight of the compost.

10. A method for cultivating plants, which comprises applying the compost of above 4 to the soil of farms or developed lands, and cultivating plants on the soil.

BEST MODES OF CARRYING OUT THE INVENTION

In the method of the invention for producing compost that has the ability to degrade dioxins, used is a lignin-containing, plant-derived organic material for the compost.

In general, weeds and vegetable refuse that can be fermented into compost within a short period of time are much used for the material for compost that serves as a soil improver or base manure. However, as not containing a large amount of lignin, they are unsuitable for the material for the compost of the invention. Even if used, they could not attain the intended effect of the invention. A lignin-containing, plant-derived organic material is suitable for the compost of the invention. Specific examples of the material are wood, bark, bamboo, corn stems, pulp, pulp wastes, etc. For their forms, wood chips and sawdust are preferred. Also preferred are bark, bamboo and corn stems having been cut into pieces to have a length of 200 mm or so; as well as their milled powders, pulverized chips or chopped pieces.

For maturing it into compost, the compost material as above is fermented in any ordinary compost fermenter. In general, in a process of producing compost from such a compost material, microbes intrinsic in the compost material, those from the nature, or those intrinsic in additives first act on the material to ferment it, then the material is thermally fermented by thermophilic anaerobic bacteria existing therein, and after the peak stage of thermophilic fermentation, the material having been thus thermally fermented is gradually to be in the latter stage of fermentation where it receives no more heat, and finally the step of fermenting the material is completely terminated. Through the process, the compost material is matured into compost.

Also in the invention, a lignin-containing, plant-derived organic material is fermented in the same manner as above. As compared with ordinary compost materials, the lignin-containing, plant-derived organic material for use in the invention is relatively slowly matured into compost since its nitrogen content is small. Therefore, in the initial stage of fermentation, it is desirable to add thereto a fermentation promoter of, for example, animal feces, activated sludge wastes, stock farm wastes and fisheries wastes, or synthetic fertilizer such as ammonium sulfate, urea and the like that serve as a nitrogen source. With such additives being added thereto, thermophilic fermentation of the compost material can be promoted in its initial stage. The amount of the fermentation promoter to be added to the plant-derived organic material falls, for example, between 5 and 30 kg of the dry weight of animal feces per ton of the dry weight of the organic material; and the amount of the synthetic fertilizer to be added thereto falls, for example, between 5 and 30 kg per the same. In case where both the two, fermentation promoter and synthetic fertilizer are used together, the total weight of the two preferably falls between 5 and 30 kg. The fermentation promoter is preferably fed into a fermenter along with the starting, plant-derived organic material thereinto. For example, it is desirable that the compost material and the fermentation promoter are alternately piled up in a compost fermenter so that the promoter can be uniformly dispersed in the compost material in the fermenter.

During the process of thermal fermentation, the water content of the starting, plant-derived organic material to be compost is controlled to fall between 40 and 85%, preferably between 45 and 70%. In order that the compost material can undergo uniform thermal fermentation, it is desirable that the pile of the compost material in the fermenter is aerated by turning it inside out twice to ten times during the process of thermal fermentation. Though varying depending on the type of the compost material to be fermented, the type of the additive thereto and their blend ratio, the period of thermal fermentation is generally a few weeks or longer.

The process of thermal fermentation necessarily includes a step of keeping the compost material at a temperature falling between 65 and 100° C. for at least 2 hours. The reason why the compost material being fermented shall be kept at the temperature falling within that range for at least 2 hours is for preventing undesirable microbes having contaminated the compost material and the additive from growing or for killing them so that they have no more negative influences on the next step where the compost material is inoculated with fungi and the thus-inoculated fungi grow in the material.

Next, the plant-derived organic material having undergone the thermal fermentation or the thus-fermented compost material is inoculated with fungi having the ability to degrade lignin, at a temperature not higher than 65° C., and is further fermented with the fungi. The temperature at which the compost material is inoculated with such fungi shall not be higher than 65° C. This is because, at temperatures higher than it, the fungi will die. Preferably, the temperature is not higher than 50° C.

Especially preferably, the fungi having the ability to degrade lignin for use in the invention are at least one type of fungi selected from a group of fungi of the genera, Chaetomium, Penicillium and Schizophyllum. Specific examples of these fungi are *Chaetomium virescens, Chaetomium reflexum, Chaetomium piluliferum, Chaetomium thermophilum, Chaetomium gracile, Chaetomium indicum, Chaetomium globosum* and *Chaetomium dolichotrichum* that are fungi of the genus Chaetomium; *Penicillium janthinellum, Penicillium funicolosum, Penicillium asperosporum, Penicillium crustosum* and *Penicillium verruculosum* that are fungi of the genus Penicillium; and Schizophyllum commune of fungi of the genus Schizophyllum.

For cultivating the culture on which the fungi are inoculated, employable is any method of cultivating ordinary fungi. For example, on a laboratory scale, the fungi are cultivated in a potato-dextrose medium at 25° C. for 10 days. For mass-production on an industrial scale, employable is any of a method of liquid culture in a tank, and a method of solid culture using, for example, a plant-derived solid component such as whole wheat grains, or an inorganic porous carrier with sugar, nitrogen, phosphorus, minerals and the like being infiltrated thereinto. In order to make the fungi have increased dioxin degradability, it is desirable that a lignin material is added to the medium of solid culture where the fungi are cultivated. In the process of cultivating the fungi, the resulting culture is so controlled that the cell concentration therein is at least $1 \times 10^2$ cfu (colony formation unit), preferably from $1 \times 10^2$ to $1 \times 10^8$ cfu, more preferably from $1 \times 10^3$ to $1 \times 10^7$ cfu, per gram of the dry weight of the plant-derived organic material. The reason why the cell concentration is controlled to fall within the defined range is because, if it is smaller than the range, the growth of the fungi inoculated will be retarded. If so, in addition, the fungi inoculated will be difficult to grow predominantly over any other existing microbes.

The fungi to be cultivated may be any of mycelia or spores. In view of their storage stability, however, it is desirable that a culture that contains cells having well grown to have a lot of spores is first prepared, and thereafter this is inoculated on a plant-derived organic material. For this, for example, in case where the fungi are cultivated according to liquid culture, supplying a carbon source to the culture medium is stopped just before the end of culture, or the pH value of the culture medium is rapidly varied, or the amount of aeration into the culture medium is reduced, whereby the sporulation is promoted. The culture of the fungi thus obtained is preferably used in the invention.

The culture of the fungi having been thus cultivated may be directly applied to the compost material to be inoculated therewith. If desired, however, the culture may be ground or cut into pieces, or may be centrifuged or sieved to separate the cells or the spores or their mixtures from the culture, and the thus-processed culture may be applied to the compost material. Also if desired, the culture may be dried at a temperature at which the cells do not die, for example, at a temperature not higher than 50° C., and the dried culture may be applied to the compost material. For drying the culture, employable is an aeration drying method, or a freeze drying method, or a method of mixing it with a dry carrier (for example, bran, inorganic carrier, etc.) to lower its water content.

The culture of the fungi thus prepared is inoculated on a plant-derived organic material at a temperature not higher than 65° C., preferably not higher than 50° C. This is because, if the temperature of the plant-derived organic material is higher than 65° C., the fungi inoculated on the material will die. For inoculating the thus-cultivated fungi on the plant-derived organic material, the cell culture may be directly applied to the material. Apart from the direct inoculation method, the cell culture is inoculated on a plant-derived organic material having been thermally fermented or on a plant-derived solid component to thereby further grow the cells, and the culture with the thus-grown cells therein may be inoculated on the compost material. As the case may be, the compost produced according to the method of the invention may be used for cell inoculation.

The plant-derived organic material thus inoculated with the fungi is fermented at a temperature falling between 10 and 50° C. This fermentation may be effected in the same field where the compost material has been thermally fermented in the previous stage. Alternatively, the material inoculated with the fungi may be embedded in soil or may be piled up for fermenting it. In this fermentation stage, the fungi inoculated on the plant-derived organic material grow. The preferred temperature in this stage varies, depending on the type of the fungi fermented on the material. At temperatures lower than 10° C., the growing activity of the cells will be low; but at temperatures higher than 50° C., the cells except some types of fungi will die.

Preferably, the plant-derived organic material contains water to some degree. In order that the fungi inoculated thereon could be active, the water content of the plant-derived organic material preferably falls between 40 and 85% by weight, more preferably between 45 and 70% by weight. If the water content of the material is lower than 40% by weight, the growth of the fungi in the material will be retarded; but if higher than 85% by weight, the material being fermented will be readily in an anaerobic condition. In such an anaerobic condition, the inoculated fungi will die. In case where the water content of the material is high and therefore the material will be in an anaerobic condition, it is desirable that the material being fermented is aerated by turning it inside out to some degree, or by forcedly introducing air into the material so that the material could be at least in a slightly aerobic condition.

Preferably, the pH value of the plant-derived organic material being fermented falls between 4 and 9. If the pH value of the material is smaller than 4 or higher than 9, the growth of the fungi in the material will be retarded. In case where the pH value of the material being fermented oversteps the range of from 4 to 9, it is desirable that an acidic or alkaline substance such as superphosphate, calcium oxide, slaked lime or the lime is added to the material so as to control the pH value of the material, thereby creating the environment favorable to the growth of the fungi.

The compost of the invention thus produced in the manner as above contains the fungi, having a cell concentration of from $10^3$ to $10^{10}$ cfu per gram of its dry weight, and contains manure ingredients highly helpful to the growth of plants. Therefore, it is effectively utilized for good growth of plants by applying it to the soil of farms and developed lands. In the compost of the invention thus applied to the soil, the fungi act to release lignin from the ingredients of the compost, and the thus-released lignin induces an enzyme, fungi-derived lignin degrading enzymes. Accordingly, the compost shall contain the lignin degrading enzymes. The lignin degrading enzymes degrades dioxins in soil into harmless substances.

Where the compost of the invention is applied to the soil of farms or developed lands in which agricultural crops are cultivated or trees or flowers are planted, its amount may be the same as that of ordinary compost. The compost of the invention may be combined with any ordinary compost. Preferably, it may be combined with chemical fertilizer poorly toxic to fungi.

The type of agricultural crops suitable to the compost of the invention is not specifically defined. The compost may be applied to any type of ordinary farm crops including, for example, agricultural and horticultural crops such as vegetables, cereal plants, bean plants, fruit trees, etc., as well as crops for stockbreeding feed, such as grass, etc. The farm crops and feed crops cultivated by the use of the compost of the invention are free from the danger of dioxin intake thereinto, and their harvests are highly safe.

The compost of the invention is useful for tree-planting projects in land developing or civil engineering. For example, it may be blended with the soil or base for cultivating trees, plants and flowers to be planted in the area of developed lands. The trees, plants and flowers for such green zones include, for example, Alnus sieboldiana, Alnus pendula, Alnus Japonica, bush clovers, cericeas, Amorpha fruticosa, white birches, indigos, Japanese privets, Rhaphiolepis umbellata, mugworts, Japanese knotweeds, eulalias, tall fescues, perennial ryegrass, creeping red fescues, etc. The compost of the invention may be applied to the soil where such trees and others are cultivated and grown, and it acts as manure for them and degrades dioxins in the soil into harmless substances.

In addition, the compost of the invention is not limited to its application to soil where plants are cultivated, like that of ordinary compost, but may also be sprayed on the surface of the ground around garbage incineration facilities which will be much contaminated with dioxins. In the contaminated ground on which the compost has been sprayed, the fungi existing in the compost act to degrade dioxins into harmless substances.

EXAMPLES

The invention is described more concretely with reference to the following Examples.

Example 1

(1) Liquid Culture of Seed Cells:

100 ml of a liquid medium of potato-dextrose was fed into a 500-ml Meyer flask, and two 3-mmφ glass beads were put thereinto. Then, this was sterilized in an autoclave at 121° C. for 20 minutes.

Next, the Meyer flask was cooled, and one platinum loop of seed cells of *Chaetomium thermophilum* (IFO 9679) were inoculated on the medium therein. The culture with the fungi inoculated thereon was cultivated by shaking it at 40° C. and at 200 rpm.

(2) Solid Culture of Fungi:

5 parts by weight of whole barley-corns, 1 part by weight of wheat bran, 1 part by weight of rice bran, 1 part by weight of defatted soybean flour, and 12 parts by weight of tap water were mixed to prepare a solid medium. This was put into a stainless vat having a length of 40 cm, a width of 50 cm and a depth of 10 cm, to the depth of 5 cm, and sterilized with steam at 121° C. for 20 minutes.

Next, the solid medium was cooled to room temperature, and 100 ml of the culture prepared in (1) was put thereinto. Then, this was incubated in a thermostat set at 40° C. The cell concentration in the thus-incubated solid culture is shown in Table 1. The cell concentration in Table 1 is in terms of the number of colony formation units (cfu) per gram of the dry weight of the solid culture.

(3) Production of Compost:

100 parts by weight of bark chips prepared by grinding the bark of a Japanese cedar in a grinder, 10 parts by weight of bovine feces and 1 part by weight of ammonium sulfate fertilizer were used herein for producing compost. The total volume of these materials was 40 $m^3$. The bark chips, bovine feces and ammonium sulfate fertilizer were alternately piled up in a roofed compost shed, in which they were thermally fermented. Two days after the start of the thermal fermentation, the temperature of the center of the pile reached 52° C.; and four days, it reached 69° C. Accordingly, the pile was aerated by turning it inside out at a frequency of once a week after the start of the fermentation. Immediately after the pile was aerated in that manner, it was wetted by sprinkling water thereon.

Nine weeks after the start of the fermentation, the pile gave no more heat, and the temperature of its center lowered to 45° C. In this stage, 1 kg of the cell culture of fungi prepared in (2) was inoculated on the pile. Immediately after having been inoculated with the cell culture, the temperature of the pile increased up to 50° C., but thereafter it gradually lowered. After 12 weeks, the temperature of the pile was 38° C.

The cell concentration of fungi in the thus-produced compost is as in Table 1. The cell concentration in Table 1 is in terms of the number of colony formation units (cfu) per gram of the dry weight of the compost.

(4) Confirmation of Lignin Degrading Enzymes Production:

A liquid medium was prepared, which contained the following components per liter of water therein and had pH of 5.1.

| | |
|---|---|
| $KH_2PO_4$ | 3.3 g |
| $MgSO_4$ | 0.8 g |
| $CaCl_2$ | 0.17 g |
| Glucose | 10.0 g |
| Ammonium tartrate | 0.22 g |
| Sodium acetate | 1.64 g |
| Micro nutrient | 100 ml |

The micro nutrient comprised the following components per liter of water therein.

| | |
|---|---|
| $MgSO_4$ | 3 g |
| $MnSO_4$ | 0.5 g |
| NaCl | 1 g |
| $FeSO_4.7H_2O$ | 0.1 g |
| $CoCl_2$ | 0.1 g |
| $ZnSO_4.7H_2O$ | 0.1 g |
| $CuSO_4$ | 0.1 g |
| $H_3BO_4$ | 0.01 g |
| $NaMoO_4.2H_2O$ | 0.01 g |

100 ml of the liquid medium was put into a 500-ml Erlenmeyer flask. On the other hand, one platinum loop of the cells of *Chaetomium thermophilum* (IFO 9679) that had been cultivated by liquid culture in above (1) were inoculated on a potato-dextrose-agar medium put in a laboratory dish, and incubated in the medium at 40° C. Discs having a diameter of 7 mm were taken out of the culture by the use of a cork borer, and three of them were put into the liquid medium in the flask, and incubated therein at 40° C. for 7 days with shaking.

Next, 10 ml of an aqueous solution of 10 wt. % glucose that had been filtered to remove germs was added to the cell culture, and this was further incubated for 1 day with shaking. Next, orthotoluidine to be 0.1 g/liter was added thereto, and this was still further incubated for 14 days with shaking. After having been thus incubated, the supernatant of the culture was taken out.

Next, 0.1 ml of a coloring reagent for lignin peroxidase and manganese peroxidase, 0.015 ml of a substrate liquid and 0.05 ml of the culture supernatant were put into a 96-well micro-plate, and reacted at 40° C. for 30 minutes. As a result, the liquid in the micro-plate turned green, indicating the presence of lignin peroxidase and manganese peroxidase therein (these are enzymes that participate in lignin degradation). The coloring reagent used herein is a solution of 2,2'-azino-bis (3-ethylbenzothiazoline-6-sulfonic acid) dissolved in 100 mM phosphoric acid-citric acid buffer (pH: 5.5) to have a concentration of 400 mg/liter. The substrate liquid used herein is aqueous hydrogen peroxide having a concentration of 0.03% by weight.

On the other hand, 0.1 ml of a coloring reagent for laccase and 0.05 ml of the culture supernatant were put into a different 96-well micro-plate, and reacted at 40° C. for 1 hour. As a result, the liquid in the micro-plate turned brown, indicating the presence of laccase therein. The coloring reagent for laccase used herein is a solution of tannic acid dissolved in 100 mM phosphoric acid-citric acid buffer (pH: 5.5) to have a concentration of 0.2% by weight.

(5) Confirmation of Dioxin Degradability:

100 ml of the same liquid medium as in above (4) was put into a 500-ml Erlenmeyer flask. On the other hand, one platinum loop of the cells of *Chaetomium thermophilum* (IFO 9679) that had been cultivated by liquid culture in above (1) were inoculated on a potato-dextrose-agar medium put in a laboratory a dish, and incubated in the medium at 40° C. Discs having a diameter of 7 mm were taken out of the culture by the use of a cork borer, and three of them were put into the liquid medium in the flask, and incubated therein at 40° C. for 7 days with shaking.

Next, 10 ml of an aqueous solution of 10 wt. % glucose that had been filtered to remove germs was added to the cell culture, and this was further incubated for 1 day with shaking. Next, 3 ng of 2,3,7,8-tetrachlorodibenzo-p-dioxin was added thereto, and this was still further incubated at 40° C. for 14 days with shaking.

After having been thus incubated, the culture was recovered. From the yield of the culture and the concentration of 2,3,7,8-tetrachlorodibenzo-p-dioxin in the culture analyzed, the degree of decomposition of 2,3,7,8-tetrachlorodibenzo-p-dioxin in the culture was obtained, and it was 24%. The culture was analyzed for the concentration of 2,3,7,8-tetrachlorodibenzo-p-dioxin therein through gas chromatography and GC-MS (gas chromatographic mass spectrometry).

Example 2

(1) Liquid Culture of Seed Cells:

A seed cell culture was prepared in the same manner as in the step (1) in Example 1. In this, however, one platinum loop of seed cells of *Penicillium janthinellum* (ATCC 44750) were cultivated at 30° C.

(2) Solid Culture of Fungi:

A solid culture of the fungi was prepared in the same manner as in the step (2) in Example 1. In this, however, the seed culture prepared in the previous step (1) was incubated at 30° C. The cell concentration in the thus-incubated solid culture is shown in Table 1.

(3) Production of Compost:

Compost was produced in the same manner as in the step (3) in Example 1. In this, however, the compost material having been thermally fermented as in the step (3) in Example 1 was inoculated with 2 kg of the solid culture prepared in the previous step (2), and further fermented at 27° C. The cell concentration of fungi in the compost produced herein is as in Table 1.

(4) Confirmation of Lignin Degrading Enzymes Production:

In the same manner as in the step (4) in Example 1, the cells of *Penicillium janthinellum* (ATCC 44750) having been cultivated in the previous step (1) were incubated at 30° C. in the same liquid medium as that in the step (4) of Example 1.

Next, the cell culture was reacted with a substrate at 30° C., using the same coloring reagents as in the step (4) in Example 1, to thereby confirm the presence of lignin degrading enzymes in the culture. As a result, the culture turned green, indicating the presence of lignin peroxidase and manganese peroxidase therein; and turned brown, indicating the presence of laccase therein.

(5) Confirmation of Dioxin Degradability:

In the same manner as in the step (5) in Example 1, the cells of *Penicillium janthinellum* (ATCC 44750) having been cultivated in the previous step (1) were incubated at 30° C. in the same liquid medium as that in the step (5) of Example 1.

Next, also in the same manner as in the step (5) of Example 1, 2,3,7,8-tetrachlorodibenzo-p-dioxin was added to the resulting cell culture, and this was further incubated at 30° C. The culture was then analyzed for the concentration of the compound therein. From the data obtained, the degree of decomposition of 2,3,7,8-tetrachlorodibenzo-p-dioxin in the culture was obtained, and it was 22%.

Example 3

(1) Liquid Culture of Seed Cells:

A seed cell culture was prepared in the same manner as in the step (1) in Example 1. In this, however, one platinum loop of seed cells of *Schizophyllum commune* (IFO 6505) were cultivated at 30° C.

(2) Solid Culture of Fungi:

A solid culture of the fungi was prepared in the same manner as in the step (2) in Example 1. In this, however, the seed culture prepared in the previous step (1) was incubated at 30° C. The cell concentration in the thus-incubated solid culture is shown in Table 1.

(3) Production of Compost:

Compost was produced in the same manner as in the step (3) in Example 1. In this, however, the compost material having been thermally fermented as in the step (3) in Example 1 was inoculated with 5 kg of the solid culture prepared in the previous step (2), and further fermented at 27° C. The cell concentration of fungi in the compost produced herein is as in Table 1.

(4) Confirmation of Lignin Degrading Enzymes Production:

In the same manner as in the step (4) in Example 1, the cells of *Schizophyllum commune* (IFO 6505) having been cultivated in the previous step (1) were incubated at 30° C. in the same liquid medium as that in the step (4) of Example 1.

Next, the cell culture was reacted with a substrate at 30° C., using the same coloring reagents as in the step (4) in Example 1, to thereby confirm the presence of lignin degrading enzymes in the culture. As a result, the culture turned green, indicating the presence of lignin peroxidase and manganese peroxidase therein; and turned brown, indicating the presence of laccase therein.

(5) Confirmation of Dioxin Degradability:

In the same manner as in the step (5) in Example 1, the cells of *Schizophyllum commune* (IFO 6505) having been cultivated in the previous step (1) were incubated at 30° C. in the same liquid medium as that in the step (5) of Example 1.

Next, also in the same manner as in the step (5) of Example 1, 2,3,7,8-tetrachlorodibenzo-p-dioxin was added to the resulting cell culture, and this was further incubated at 30° C. The culture was then analyzed for the concentration of the compound therein. From the data obtained, the degree of decomposition of 2,3,7,8-tetrachlorodibenzo-p-dioxin in the culture was obtained, and it was 33%.

Example 4

(1) Liquid Culture of Seed Cells:

A seed cell culture was prepared in the same manner as in the step (1) in Example 1. In this, however, one platinum loop of seed cells of *Chaetomium virescens* (ATCC 32319) were cultivated.

(2) Solid Culture of Fungi:

A solid culture of the fungi was prepared in the same manner as in the step (1) in Example 1. In this, however, the seed culture prepared in the previous step (1) was incubated. The cell concentration in the thus-incubated solid culture is shown in Table 1.

(3) Production of Compost:

Compost was produced in the same manner as in the step (3) in Example 1. In this, however, the compost material having been thermally fermented as in the step (3) in Example 1 was inoculated with 2 kg of the solid culture prepared in the previous step (2), and further fermented at

Example 5

(1) Liquid Culture of Seed Cells:

A seed cell culture was prepared in the same manner as in the step (1) in Example 1. In this, however, one platinum loop of seed cells of *Chaetomium reflexum* (ATCC 16213) were cultivated.

(2) Solid Culture of Fungi:

A solid culture of the fungi was prepared in the same manner as in the step (2) in Example 1. In this, however, the seed culture prepared in the previous step (1) was incubated. The cell concentration in the thus-incubated solid culture is shown in Table 1.

(3) Production of Compost:

Compost was produced in the same manner as in the step (3) in Example 1. In this, however, the compost material having been thermally fermented as in the step (3) in Example 1 was inoculated with 2 kg of the solid culture prepared in the previous step (2), and further fermented at 37° C. The cell concentration of fungi in the compost produced herein is as in Table 1.

Example 6

(1) Liquid Culture of Seed Cells:

A seed cell culture was prepared in the same manner as in the step (1) in Example 1. In this, however, one platinum loop of seed cells of *Chaetomium piluliferum* (ATCC 16221) were cultivated.

(2) Solid Culture of Fungi:

A solid culture of the fungi was prepared in the same manner as in the step (2) in Example 1. In this, however, the seed culture prepared in the previous step (1) was incubated. The cell concentration in the thus-incubated solid culture is shown in Table 1.

(3) Production of Compost:

Compost was produced in the same manner as in the step (3) in Example 1. In this, however, the compost material having been thermally fermented as in the step (3) in Example 1 was inoculated with 1 kg of the solid culture prepared in the previous step (2), and further fermented at 37° C. The cell concentration of fungi in the compost produced herein is as in Table 1.

Example 7

(1) Liquid Culture of Seed Cells:

A seed cell culture was prepared in the same manner as in the step (1) in Example 1. In this, however, one platinum loop of seed cells of *Chaetomium piluliferum* (ATCC 32782) were cultivated.

(2) Solid Culture of Fungi:

A solid culture of the fungi was prepared in the same manner as in the step (2) in Example 1. In this, however, the seed culture prepared in the previous step (1) was incubated. The cell concentration in the thus-incubated solid culture is shown in Table 1.

(3) Production of Compost:

Compost was produced in the same manner as in the step (3) in Example 1. In this, however, the compost material having been thermally fermented as in the step (3) in Example 1 was inoculated with 2 kg of the solid culture prepared in the previous step (2), and further fermented at 37° C. The cell concentration of fungi in the compost produced herein is as in Table 1.

Example 8

(1) Liquid Culture of Seed Cells:

A seed cell culture was prepared in the same manner as in the step (1) in Example 1. In this, however, one platinum loop of seed cells of *Chaetomium thermophilum* (IFO 30072) were cultivated.

(2) Solid Culture of Fungi:

A solid culture of the fungi was prepared in the same manner as in the step (2) in Example 1. In this, however, the seed culture prepared in the previous step (1) was incubated. The cell concentration in the thus-incubated solid culture is shown in Table 1.

(3) Production of Compost:

Compost was produced in the same manner as in the step (3) in Example 1. In this, however, the compost material having been thermally fermented as in the step (3) in Example 1 was inoculated with 2 kg of the solid culture prepared in the previous step (2), and further fermented. The cell concentration of fungi in the compost produced herein is as in Table 1.

Example 9

(1) Liquid Culture of Seed Cells:

A seed cell culture was prepared in the same manner as in the step (1) in Example 1. In this, however, one platinum loop of seed cells of *Chaetomium thermophilum* (IFO 30073) were cultivated.

(2) Solid Culture of Fungi:

A solid culture of the fungi was prepared in the same manner as in the step (2) in Example 1. In this, however, the seed culture prepared in the previous step (1) was incubated. The cell concentration in the thus-incubated solid culture is shown in Table 1.

(3) Production of Compost:

Compost was produced in the same manner as in the step (3) in Example 1. In this, however, the compost material having been thermally fermented as in the step (3) in Example 1 was inoculated with 2 kg of the solid culture prepared in the previous step (2), and further fermented. The cell concentration of fungi in the compost produced herein is as in Table 1.

TABLE 1

| Example | Type of Fungi | Seed Cell Concentration (cfu/g) | Cell Concentration in Compost (cfu/g) |
|---|---|---|---|
| 1 | *Chaetomium thermophilum* (IFO 9679) | $5.3 \times 10^8$ | $1.1 \times 10^7$ |
| 2 | *Penicillium janthinellum* (ATCC 44750) | $2.9 \times 10^8$ | $9.8 \times 10^6$ |
| 3 | *Schizophyllum commune* (IFO 6505) | $3.1 \times 10^7$ | $6.9 \times 10^6$ |
| 4 | *Chaetomium virescens* (ATCC 32319) | $7.2 \times 10^8$ | $2.6 \times 10^7$ |
| 5 | *Chaetomium reflexum* (ATCC 16213) | $4.4 \times 10^8$ | $1.9 \times 10^6$ |
| 6 | *Chaetomium piluliferum* (ATCC 16221) | $1.2 \times 10^9$ | $2.3 \times 10^7$ |
| 7 | *Chaetomium piluliferum* (ATCC 32782) | $4.0 \times 10^8$ | $5.5 \times 10^5$ |

TABLE 1-continued

| Example | Type of Fungi | Seed Cell Concentration (cfu/g) | Cell Concentration in Compost (cfu/g) |
|---|---|---|---|
| 8 | Chaetomium thermophilum (IFO 30072) | $9.6 \times 10^8$ | $5.4 \times 10^6$ |
| 9 | Chaetomium thermophilum (IFO 30073) | $7.8 \times 10^8$ | $1.1 \times 10^7$ |

Example 10

(1) Liquid Culture of Seed Cells:

A seed cell culture was prepared in the same manner as in the step (1) in Example 1. In this, however, one platinum loop of seed cells of Chaetomium thermophilum (IFO 9679) were cultivated.

(2) Solid Culture of Fungi:

5 parts by weight of whole barley-corns, 1 part by weight of wheat bran, 1 part by weight of chips of cherry wood, 1 part by weight of defatted soybean flour, and 20 parts by weight of aqueous 0.6% potato-dextrose solution were mixed to prepare a solid medium. This was put into a stainless vat having a length of 40 cm, a width of 50 cm and a depth of 10 cm, to the depth of 5 cm, and sterilized with steam at 121° C. for 20 minutes.

Next, the solid medium was cooled to room temperature, and 100 ml of the culture prepared in (1) was put thereinto. Then, this was incubated in a thermostat set at 40° C. The cell concentration in the thus-incubated solid culture was $3.2 \times 10^8$ cfu/g. The cell concentration is in terms of the number of colony formation units (cfu) per gram of the dry weight of the solid culture.

(3) Confirmation of Dioxin Degradability in Soil:

Black soil was collected from a mountain, and sterilized with steam at 121° C. for 20 minutes. Next, 6 types of dioxins shown in Table 2 were added to the sterilized soil, and well stirred. The dioxin-contaminated soil was inoculated with the solid culture prepared in above (2) to have a different cell concentration of $1 \times 10$, $5 \times 10^2$ or $1 \times 10^5$ cfu per gram of the dry weight of the soil, and then uniformly mixed. The soil was then kept in a thermostat at 30° C. for 1 month, with stirring it once a day, whereby the dioxins in the soil were degraded by the fungi therein. After having been thus processed, the dioxins were extracted out of the soil and analyzed. The data obtained are given in Table 2.

Example 11

(1) Liquid Culture of Seed Cells:

A seed cell culture was prepared in the same manner as in the step (1) in Example 1. In this, however, one platinum loop of seed cells of Penicillium janthinellum (ATCC 44750) were cultivated at 30° C.

(2) Solid Culture of Fungi:

A solid culture of the fungi was prepared in the same manner as in the step (2) in Example 10. In this, however, the seed culture prepared in the previous step (1) was incubated at 30° C. The cell concentration in the thus-incubated solid culture was $3.6 \times 10^8$ cfu/g.

(3) Confirmation of Dioxin Degradability in Soil:

Dioxins in soil were degraded in the same manner as in the step (3) of Example 10. In this, however, the cells of Penicillium janthinellum (ATCC 44750) having been cultivated in the previous step (1) were incubated at 30° C. in the same solid medium as in the step (2) of Example 10, and the resulting solid culture was inoculated on the soil.

Like in Example 10, the dioxins were extracted out of the thus-processed soil and analyzed. The data obtained are given in Table 2.

Example 12

(1) Liquid Culture of Seed Cells:

A seed cell culture was prepared in the same manner as in the step (1) in Example 1. In this, however, one platinum loop of seed cells of Schizophyllum commune (IFO 6505) were cultivated at 30° C.

(2) Solid Culture of Fungi:

A solid culture of the fungi was prepared in the same manner as in the step (2) in Example 10. In this, however, the seed culture prepared in the previous step (1) was incubated at 30° C. The cell concentration in the thus-incubated solid culture was $6.7 \times 10^7$ cfu/g.

(3) Confirmation of Dioxin Degradability in Soil:

Dioxins in soil were degraded in the same manner as in the step (3) of Example 10. In this, however, the cells of Schizophyllum commune (IFO 6505) having been cultivated in the previous step (1) were incubated at 30° C. in the same solid medium as in the step (2) of Example 10, and the resulting solid culture was inoculated on the soil.

Like in Example 10, the dioxins were extracted out of the thus-processed soil and analyzed. The data obtained are given in Table 2.

TABLE 2

Result of Test for Dioxin Degradation in Soil with Microorganisms

| Dioxins | Before Processed | Control | $1.0 \times 10$ cfu/g | $5.0 \times 10^2$ cfu/g | $1.0 \times 10^5$ cfu/g |
|---|---|---|---|---|---|
| | | Chaetomium thermophilum IFO 9679 | | | |
| | | | Chaetomium thermophilum | Chaetomium thermophilum | Chaetomium thermophilum |
| 2,3,7,8-TCDD | 10 | 9 | 10 | 7 | 6 |
| 1,3,6,8-TCDD | 1235 | 1105 | 1092 | 853 | 844 |
| 1,3,7,9-TCDD | 471 | 420 | 433 | 376 | 339 |
| 1,2,3,7,8-PCDD | 5 | 5 | 5 | 3 | 3 |
| 1,2,3,6,7,8-HCDD | 19 | 14 | 14 | 5 | 4 |
| 2,3,7,8-TCDF | 10 | 8 | 9 | 7 | 7 |
| Total | 1750 | 1561 | 1563 | 1251 | 1203 |
| Degree of Degradation (%) | 0.0 | 10.8 | 10.7 | 28.5 | 31.3 |

TABLE 2-continued

Result of Test for Dioxin Degradation in Soil with Microorganisms

| Dioxins | Before Processed | Control | $1.0 \times 10$ cfu/g | $5.0 \times 10^2$ cfu/g | $1.0 \times 10^5$ cfu/g |
|---|---|---|---|---|---|
| | | *Penicillium janthinellum* ATCC 44750 | | | |
| | | | *Penicillium janthinellum* | *Penicillium janthinellum* | *Penicillium janthinellum* |
| 2,3,7,8-TCDD | 10 | 9 | 9 | 8 | 9 |
| 1,3,6,8-TCDD | 1235 | 1105 | 1112 | 920 | 924 |
| 1,3,7,9-TCDD | 471 | 420 | 431 | 359 | 340 |
| 1,2,3,7,8-PCDD | 5 | 5 | 5 | 4 | 4 |
| 1,2,3,6,7,8-HCDD | 19 | 14 | 14 | 6 | 7 |
| 2,3,7,8-TCDF | 10 | 8 | 8 | 7 | 7 |
| Total | 1750 | 1561 | 1579 | 1304 | 1291 |
| Degree of Degradation (%) | 0.0 | 10.8 | 9.8 | 25.5 | 26.2 |
| | | *Schizophyllum commune* IFO 6505 | | | |
| | | | *Schizophyllum commune* | *Schizophyllum commune* | *Schizophyllum commune* |
| 2,3,7,8-TCDD | 10 | 9 | 9 | 6 | 5 |
| 1,3,6,8-TCDD | 1235 | 1105 | 1057 | 842 | 840 |
| 1,3,7,9-TCDD | 471 | 420 | 409 | 315 | 317 |
| 1,2,3,7,8-PCDD | 5 | 5 | 5 | 3 | 2 |
| 1,2,3,6,7,8-HCDD | 19 | 14 | 13 | 3 | 7 |
| 2,3,7,8-TCDF | 10 | 8 | 9 | 6 | 5 |
| Total | 1750 | 1561 | 1502 | 1175 | 1176 |
| Degree of Degradation (%) | 0.0 | 10.8 | 14.2 | 32.9 | 32.8 | unit: pg/g

TCDD: Tetrachlorodibenzo-p-dioxin
PCDD: Pentachlorodibenzo-p-dioxin
HCDD: Hexachlorodibenzo-p-dioxin
TCDF: Tetrachlorodibeozofuran

INDUSTRIAL APPLICABILITY

As described in detail hereinabove, the fungi, the substances inoculated with them and the compost of the invention have the ability to degrade dioxins in soil, such as that in farms for farm crops or feed crops or in developed lands where trees, plants and flowers are to be planted, into harmless substances. According to the method of the invention, the compost having the ability to degrade dioxins can be, produced efficiently.

What is claimed is:

1. A method of degrading dioxins, comprising contacting at least one fungi of a genus selected from the group consisting of Chaetomium and Schizophyllum to a dioxin-containing organic or inorganic substance.

2. The method of claim 1, wherein the fungi is in an amount of at least $1 \times 10^2$ cfu per gram of the dry weight of the substance.

3. The method of claim 1, wherein the fungi is contained in a material inoculated with the fungi.

4. The method of claim 3, wherein the fungi-inoculated material is a compost containing at least one fungi, which degrades lignin and dioxin, that belongs to a genus selected from the group consisting of Chaetomium and Schizophyllum.

5. A method of degrading dioxins, comprising contacting at least one fungi selected from the group consisting of *Penicillium janthinellum, Penicillium funicolosum, Penicillium asperosporum, Penicillin crustosum*, and *Penicillium verruculosum* to a dioxin-containing organic or inorganic substance to form a fungi-inoculated material.

6. The method of claim 5, wherein the fungi is contained in a material inoculated with the fungi.

7. The method of claim 5, wherein the fungi is in an amount of at least $1 \times 10^2$ cfu per gram of the dry weight of the substance.

8. The method of claim 7, wherein the fungi-inoculated material is a compost containing at least one fungi, which degrades lignin and dioxin, that is selected from the group consisting of *Penicillium janthinellum, Penicillium funicolosum, Penicillium asperosporum, Penicillin crustosum*, and *Penicillium verruculosum*.

9. A method for producing a compost comprising fermenting a plant-derived organic material comprising lignin by maintaining the temperature between 65 and 100° C. for at least 2 hours, inoculating the plant-derived organic material with at least one type of fungi that degrades lignin and belongs to a genus selected from the group consisting of Chaetomium, Penicillium, and Schizophyllum, and further fermenting said plant-derived organic material at a temperature not higher than 65° C.

10. The method of claim 9, wherein the cell concentration of the fungi is $1 \times 10^3$ to $1 \times 10^{10}$ cfu per gram of the dry weight of the compost.

11. A method for cultivating plants, which comprises producing a compost by the process of claim 9, applying the compost to a soil of farms or developed lands, and cultivating plants on the soil.

12. The method of claim 9, wherein said fermenting a plant-derived organic material is in the presence of a fermentation-promoting nitrogen fertilizer component.

13. The method of claim 12, wherein the cell concentration of the fungi is $1 \times 10^3$ to $1 \times 10^{10}$ cfu per gram of the dry weight of the compost.

14. A method for cultivating plants, which comprises producing a compost by the process of claim 12, applying the compost to a soil of farms or developed lands, and cultivating plants on the soil.

15. The method of claim 12, wherein said fermentation-promoting nitrogen fertilizer is one or more fertilizers selected from the group consisting of animal feces, activated sludge waste, stock farm waste, fishery waste, and a synthetic fertilizer.

16. The method of claim 15, wherein said fermentation-promoting nitrogen fertilizer is animal feces.

17. The method of claim 16, wherein said animal feces is added in an amount of 5 to 30 kg of dry weight of said animal feces per ton of dry weight of said plant-derived organic material.

18. The method of claim 15, wherein said fermentation-promoting nitrogen fertilizer is a synthetic fertilizer.

19. The method of claim 18, wherein said synthetic fertilizer is ammonium sulfate or urea.

20. The method of claim 18, wherein said synthetic fertilizer is added in an amount of 5 to 30 kg of dry weight of said synthetic fertilizer per ton of dry weight of said plant-derived organic material.

* * * * *